United States Patent [19]

Yan

[11] Patent Number: 4,899,017
[45] Date of Patent: Feb. 6, 1990

[54] PROCESS FOR THE SELECTIVE SEPARATION OF PARA-XYLENE FROM C8 AROMATIC MIXTURES

[75] Inventor: Tsoung Y. Yan, Philadelphia, Pa.
[73] Assignee: Mobil Oil Corporation, New York, N.Y.
[21] Appl. No.: 78,440
[22] Filed: Jul. 27, 1987
[51] Int. Cl.$^4$ .............................................. C07C 7/12
[52] U.S. Cl. ..................................... 585/828; 585/826; 208/310 Z
[58] Field of Search ........................ 505/820, 826, 828; 208/310 Z

[56] References Cited

U.S. PATENT DOCUMENTS

| | | | |
|---|---|---|---|
| 2,921,970 | 1/1960 | Gillmore | 208/310 Z |
| 3,242,070 | 3/1966 | Epperly et al. | 208/310 Z |
| 3,699,182 | 10/1972 | Cattanach | 208/30 Z |
| 3,770,842 | 11/1973 | Meyers, Jr. | 585/828 |
| 3,943,182 | 3/1976 | Neuzil | 260/674 SA |
| 3,997,620 | 12/1976 | Neuzil | 260/674 SA |
| 3,998,901 | 12/1976 | Neuzil | 260/674 SA |
| 4,021,499 | 5/1977 | Bieser | 260/674 SA |
| 4,309,281 | 1/1982 | Dessau | 208/310 Z |
| 4,351,981 | 9/1982 | Smolin | 585/828 |
| 4,423,280 | 12/1983 | Dessau | 208/310 Z |
| 4,453,029 | 6/1984 | Dessau | 585/828 |
| 4,705,909 | 11/1987 | Yan | 585/828 |

FOREIGN PATENT DOCUMENTS

| | | |
|---|---|---|
| 2420304 | 11/1974 | Fed. Rep. of Germany . |
| 2738518 | 8/1977 | Fed. Rep. of Germany . |
| 2934768 | 3/1980 | Fed. Rep. of Germany . |
| 52-00937 | 1/1977 | Japan . |
| 52-87123 | 7/1977 | Japan . |
| 52-42781 | 10/1977 | Japan . |

OTHER PUBLICATIONS

Broughton, D. B., et al., "The Parex Process for Recovering Para Xylene" CEP. 66 70–75, #9, (1970).
Chemical Engineering Progress, vol. 66, No. 9, Sep. 1970, p. 70.

Primary Examiner—Glenn Caldarola
Attorney, Agent, or Firm—Alexander J. McKillop; Charles J. Speciale; Marina V. Schneller

[57] ABSTRACT

A process scheme for the recovery of high purity p-xylene or p-xylene and ethyl benzene from C$_8$ aromatics is described. In the process, zeolites such as ZSM-5 type, zeolite beta and ZSM-11 with optimum silica alumina ratio is used as the adsorbent and light hydrocarbons, such as C$_5$ is used as the desorbent. The process system is operated isothermally at low temperature and low pressures.

13 Claims, 1 Drawing Sheet

PROCESS FOR THE SELECTIVE SEPARATION OF PARA-XYLENE FROM C8 AROMATIC MIXTURES

FIELD OF THE INVENTION

The invention relates to a process for the selective separation of xylene isomers. Particularly, the invention relates to a method of selectively separating para-xylene from $C_8$ aromatic mixtures and also relates to an improved method for separating para-xylene and ethyl benzene from $C_8$ aromatic mixtures.

BACKGROUND OF THE INVENTION

Para-xylene is a commodity which can be retreived from $C_8$ aromatic mixtures containing the same. The $C_8$ aromatic mixtures include ethyl benzene and the xylene isomers ortho-xylene, meta-xylene and para-xylene. The patent literture describes various processes for increasing the para-xylene content of such $C_8$ aromatic mixtures, for example, by xylene isomerization processes.

Para-xylene is a raw material, supplied in $C_8$ aromatic mixtures from naphtha-crackers or the disproportionation of toluene, as well as by reforming processes.

Para-xylene is the most valuable commodity of the $C_8$ aromatic mixture fractions because it is a direct precursor in the production of terephthalic acid and dimethylterephthalic, each of which can be used to produce polyester, polyester fiber and films.

Ethyl benzene, the intermediate in synthesis of styrene, is a valuable commodity and is often contained in the $C_8$ aromatic mixtures. Recovery of ethyl benzene is desirable but extremely difficult. As a result, ethyl benzene is often converted to benzene, toluene and xylenes at high severity conditions.

One of the problems which inheres in the production of para-xylene is its isolation from a typical $C_8$ aromatic mixture. Prior art processes for separating para-xylene from a $C_8$ aromatic mixture, also containing ortho-xylene, meta-xylene and ethyl benzene have been described. Those processes are cumbersome, because of the physical properties of the components of the $C_8$ aromatic mixtures are very similar. For example, ortho-xylene, has a boiling point 3.5° C. higher than tht of its closest boiling $C_8$ aromatic isomer (meta-xylene); conventional fractional distillation techniques to separate ortho-xylene from meta-xylene include fractional distillation towers which contain 100 to 150 trays and operate at about a 5–8 to 1 reflux ratio. Ethyl benzene can be separated from such mixtures, but because its boiling point is 2° C. different from the boiling point of para-xylene, the typical ethyl benzene fractionator contains 300–400 actual trays and requires about a 25–50 to 1 reflux to feed ratio. Since the meta- and para-xylene differ by only 0.7° C. in boiling point, separation of these isomers by distillation is virtually impractical.

SUMMARY OF THE INVENTION

The invention relates to recovery of high purity para-xylene and/or para-xylene and ethyl benzene from $C_8$ aromatic mixtures, by selective adsorption methods.

The separation involves two steps: (1) contacting the feed stream comprising the $C_8$ aromatic mixtures with an adsorbent selective for para-xylene; and (2) upon separating the raffinate from the adsorbent, contacting the adsorbent with a nonaqueous desorbent to recover para-xylene from the adsorbent.

In accordance with the invention, the process can be undertaken with chemically stable, inexpensive materials acting as a desorbent; separation of the xylene can be undertaken at low temperatures. The process can be undertaken in units operated isothermally at low temperatues and pressures, thereby resulting in savings of capital and energy costs.

DESCRIPTION OF THE INVENTION

Figure 1:
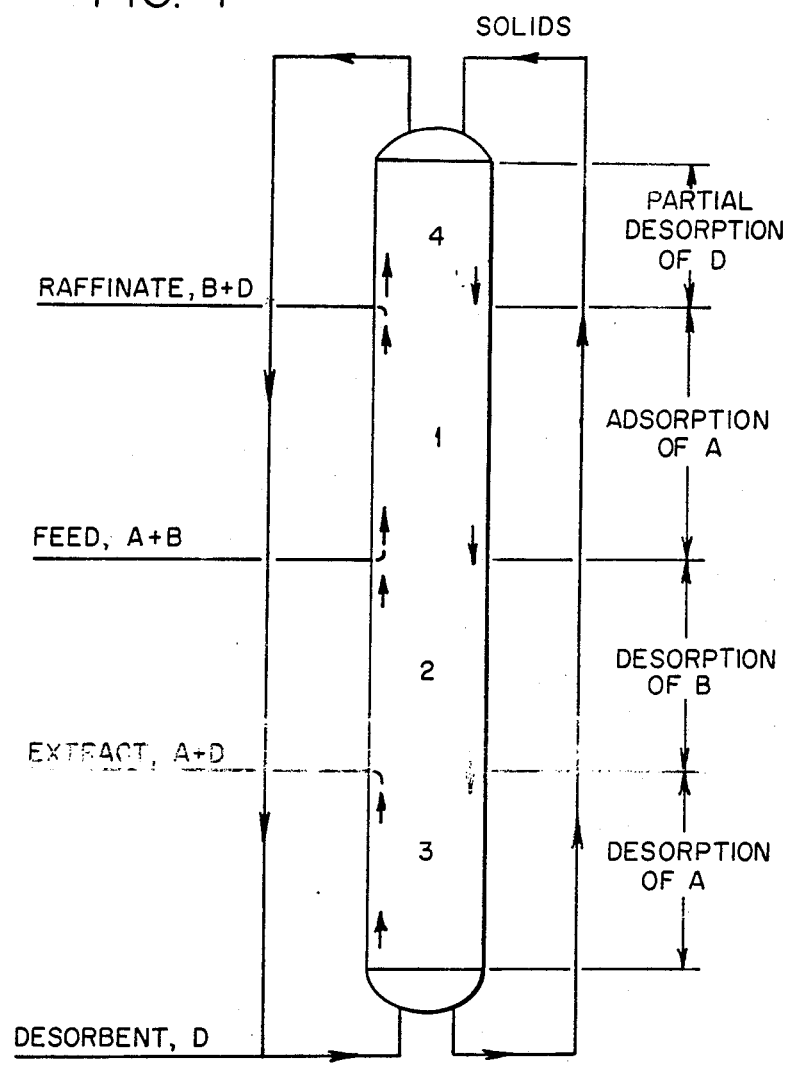
FIG. 1 is a schematic diagram of a continuous adsorption-desorption process in accordance with the invention.

A liquid fraction comprising $C_8$ aromatics, which include para-xylene, admixed with at least one other $C_8$ aromatic selected from the group consisting of ethyl benzene, ortho-xylene, meta-xylene or admixtures thereto is contacted with a zeolitic desorbent.

The zeolite desorbent is preferably ZSM-5, ZSM-11 or zeolite beta. These zeolites are known zeolites and described in U.S. Pat. Nos. 3,702,886 and Re 29948 (ZSM-5); 3,709,979 (ZSM-11) and 3,308,069 (zeolite beta). Those zeolites are identified by their X-ray diffraction patterns, which are described in those U.S patents which are incorporated by reference herein, particularly with respect to the X-ray diffraction patterns.

Preferably, the zeolites used in the process have a high silica:alumina ratio. Preferred silica-alumina ratio of the zeolitic adsorbent varies with the particular zeolite. If the zeolite is ZSM-5, preferably the silica-alumina ratio is 200 to 2000; if the zeolitic adsorbent is ZSM-11, preferably the silica:alumina ratio is 100 to 4000. If the zeolitic adsorbent is zeolite beta, preferably the silica:alumina ratio is 10 to 500. These three zeolites exhibit high capacity and selectivity. The crystal sizes of the zeolitic desorbent can be between 0.001 to 15 mm and preferably 0.001 to 10 mm. Most preferably, the crystal sizes of the zeolitic desorbent are of uniform size distribution.

The zeolitic adsorbent can be formd into particles of 0.005 to 0.5 microns in diameter and may be in the form of spheres or cylinders, or other shapes. Formation of the zeolitic adsorbent into particles can be by way of extrusion, spray drying as well as other conventional means.

The adsorbents can be in the acid form or can be exchanged with cations to reduce the acidity thereof, to minimize side reactions including polymerization. When the adsorbent is ZSM-5 or ZSM-11, and is cation exchanged, preferably the cations are small cations such as lithium and sodium.

The cations should have anionic radium less than that of cesium. Cesium exchanged ZSM-5 capacity for p-xylene adsorption decreases to about one-half of the value of the ZSM-5 of cesium.

The most preferred adsorbent is ZSM-5. The selectivity of ZSM-5 catalyst of high silica alumina ratio for para xylene over ethyl benzene is high, and appears to have maximum at a $SiO_2:Al_2O_3$ mole ratio of about 300–1500 (see Table 1). The selectivity, $S_{p/e}$ *is defined as follows*:

$$S_{p/e} = \frac{[\text{P-X adsorbed, g/g}] [\text{EB conc. in liquid, g/cc}]}{[\text{P-X conc. in liquid, g/cc}] [\text{EB adsorbed, g/g}]}$$

Where
P-X is para-xylene
EB is ethyl benzene
The $S_{p/e}$, as high as 8.66, has been reached.

In TABLE 1 the para-xylene adsorption capacity and selectivity of ZSM-5 is illustrated.

TABLE 1

Para-Xylene Adsorption Capacity and Selectivity of ZSM-5

| | Feed Composition W % | | | | | |
|---|---|---|---|---|---|---|
| EB | | | | 19.5 | | |
| PX | | | | 21.3 | | |
| OX | | | | 39.7 | | |
| MT* | | | | 19.5 | | |
| Run No. | 1 | 1-1 | 2 | 3 | 4 | 5 | 6 |

| Run No. | 1 | 1-1 | 2 | 3 | 4 | 5 | 6 |
|---|---|---|---|---|---|---|---|
| Silica/Alumina ratio | 600 | 600 | 70 | 198 | 1600 | 35 | 350 |
| Eq. Composition | | | | | | | |
| EB | 19.9 | 19.8 | 18.5 | 19.2 | 19.7 | 19.03 | 19.7 |
| PX | 18.3 | 18.4 | 20.8 | 19.0 | 18.6 | 19.06 | 18.2 |
| OX | 41.4 | 41.2 | 40.5 | 41.1 | 41.1 | 41.78 | 41.3 |
| MT | 20.4 | 20.6 | 20.2 | 20.7 | 20.6 | 20.12 | 20.8 |
| Equilibrium Time, hr. | 1 | 46 | 1 | 2 | | 2 | 2 |
| Adsorption, mg/g | | | | | | | |
| EB | 14.3 | 22.7 | 49.2 | 42.4 | 25.6 | 31.7 | 30.9 |
| PX | 114.2 | 116.5 | 36.6 | 102.0 | 110.8 | 84.8 | 127.1 |
| OX | 3.8 | 21.0 | 18.1 | 29.5 | 23.8 | — | 29.4 |
| Total | 132.3 | 160.2 | 103.8 | 173.9 | 160.2 | 116.5 | 187.4 |
| Selectivity | | | | | | | |
| Sp/e | 8.66 | 5.52 | 0.66 | 2.63 | 4.59 | 2.67 | 4.45 |
| Sp/O | 67.99 | 12.42 | 3.93 | 7.49 | 10.27 | — | 9.80 |
| Se/O | 7.85 | 2.25 | | 9.29 | 3.08 | | |

*MT = Mesitylene

The zeolitic adsorbent is used in the form of a bed. the bed of zeolitic adsorbent may be a fixed bed or a moving bed system. A fixed bed system, such as is used in a chromatographic separation, will allow separation of both para-xylene and ethyl benzene. In a fixed bed system, adsorption separation involves charging alternative increments of $C_8$ aromatic feed and desorbent to the fixed bed of zeolitic adsorbent, and then withdrawing extract and raffinate products alternately from the bed outlet. As the $C_8$ aromatic mixture feed components ae washed through the bed, the components gradually separate into separate bands which travel through the bed at different rates and are withdrawn alterntely as raffinate and extract. The bands broaden as they travel down the column. In a fixed bed system, a second increment of feed must be delayed long enough to ensure that the least strongly adsorbed component does not overtake the most strongly adsorbed component in the first increment of feed.

If pure para-xylene separation is desired, it is preferred to use a moving bed system. In the moving bed system, the solid zeolitic desorbent and the liquid are conveyed substantially continuously; most preferably they are conveyed counter currently to each other. A scheme of the continuous counterflow of solid and liquid is shown in FIG. 1. FIG. 1 is adapted from a flow chart in such a system reported in *Chemical Engineering Progress* (Vol. 66, No. 9, Page 70 (September 1970)). In such a bed, external streams divide the bed into four zones, each of which performs a different function. In zone 1, para-xylene is removed completely from the liquid stream by the adsorbent and produces a stream of components including the desorbent and $C_8$ aromatic feed minus para-xylene. Solid entering zone 1 contains only desorbent and the other components of the $C_8$ aromatic mixture (minus para-xylene). As the solid moves, it picks up para-xylene from the liquid stream. Simultaneously, some of the desorbent is desorbed from the solid by para-xylene which becomes adsorbed. In zone 2, desorption of component B (the feed minus para-xylene) completely from the solid. The solid entering zone 2 carries both para-xylene and the other $C_8$ aromatic components as adsorbed components, since it has just been in contact with fresh feed. Liquid entering the bottom of the zone contains only para-xylene and desorbent. As the solid descends, the adsorbed components of the $C_8$ aromatic mixture (free of para-xylene) are gradually desorbed from the solid by the rising liquid stream of para-xylene plus desorbent. Because para-xylene is more tenaciously adsorbed than the remainder of the components, it is possible to completely accomplish the removal of the other components of the $C_8$ aromatic stream from the solid without simultaneously removing all of the adsorbed para-xylene. In zone 3, the desorptionof para-xylene occurs. The solid entering zone 3 carries para-xylene and desorbent as adsorbed components. Liquid entering the bottom contains only desorbent. As the solid descends adsorbed para-xylene is gradually desorbed by the desorbent and is removed from the system. In zone 4, partial desorption of desorbent occurs.

The conditions of the system, whether fixed bed or moving bed, are maintained isothermally at low temperature and at low pressure. Preferably, the physical conditions of temperature and pressure are no more severe than 100° C. (at atmospheric pressure). The conditions of the system are such as to maintain the desorbent in the liquid phase. Temperatures of the system range between plus or minus 5° of the boiling point of the desorbent. Pressures in adsorption range from 0 to 100 psig. Accordingly, when the desorbent is, for example, n-hexane, the system temperature preferred will be 64 to 74° C. Preferably, the adsorption temperature should be kept at or below 80° C. Above about 100° C., the adsorption capacity of the zeolitic desorbent, particularly ZSM-5, decreases.

Preferably the desorbents are normal-paraffins of 3 to 8 carbon atoms, alkyl naphthenes, wherein the alkyl contains 5 to 8 carbon atoms, benzene and toluene. When the zeolitic adsorbent is ZSM-5 or ZSM-11, n-paraffins are preferred, and most preferably it is pentane, hexane and/or the heptanes. When the zeolitic adsorbent is zeolite beta, heavy aromatics such as $C_9$–$C_{12}$ aromatics may also be used as desorbents.

What is claimed is:

1. A process for removing p-xylene from a mixture including p-xylene and at least one other $C_8$ aromatic compound selected from the group consisting of m-xylene, o-xylene and ethylene benzene, comprising contacting said mixture with a bed comprising a zeolite having a $SiO_2:Al_2O_3$ molar ratio of at least 200 selected from the group consisting of ZSM-5, ZSM-11 and zeolite beta, at a temperature up to about 100° C. (atmospheric pressure), whereby p-xylene is adsorbed by said zeolite and said at least one other $C_8$ aromatic compound passes through the bed;

passing through said bed containing the zeolite and adsorbed p-xylene, a desorbent, while maintaining the temperature the same as that used during said contacting and thereby maintaining the desorbent in the liquid state; whereby desorbent leaving the bed contains p-xylene.

2. The process of claim 1, wherein the desorbent is a paraffin having 3 to 8 carbon atoms.

3. The process of claim 1 wherein the desorbent is pentane or hexane.

4. The process of claim 1 wherein said bed is a fixed bed.

5. The process of claim 1 wherein said bed is a moving bed.

6. The process of claim 1 wherein said desorbent is passed into the bed counter currently to said mixture.

7. The process of claim 5, wherein said desorbent is passed into the bed countercurrently to said mixture.

8. The process of claim 6, wherein the zeolite is SZM-5 having a silica alumina mole ratio of at least about 200.

9. The process of claim 7 wherein the zeolite is ZSM-5 having an $SiO_2:Al_2O_3$ mole ratio of at least about 200.

10. The process of claim 8, wherein the zeolite is ZSM-5, having an $SiO_2:Al_2O_3$ mole ratio of at least about 200.

11. The process of claim 1, wherein said ZSM-5 has a $SiO_2:Al_2O_3$ ratio of about 300–1500.

12. The process of claim 6, wherein the bed comprises ZSM-5 with a silica:alumina ratio of 300 to 1500.

13. A process for recovering p-xylene substantially free of ethyl benzene from a mixture including p-xylene and at least one other $C_8$ aromatic compound selected from the group consisting of m-xylene, o-xylene and ethyl benzene, comprising continuously contacting said mixture with a moving bed comprising zeolite ZSM-5 having a silica:alumina ratio of 300 to 1500 at a temperature up to about 100° C. (atmospheric pressure), whereby p-xylene is adsorbed by said zeolite;

passing through said bed of zeolite containing adsorbed p-xylene, a desorbent, wherein the desorbent is passed in a direction countercurrently to the direction of the moving bed while maintaining the temperature the same as that used during said contacting and thereby maintaining the desorbent in the liquid state; whereby desorbent leaving the bed contains p-xylene.

* * * * *

UNITED STATES PATENT AND TRADEMARK OFFICE
CERTIFICATE OF CORRECTION

PATENT NO. : 4,899,017
DATED : February 6, 1990
INVENTOR(S) : Tsoung Y. Yan It is certified that error appears in the above-identified patent and that said Letters Patent is hereby corrected as shown below:

Col. 6, Line 8 -- change SZM-5 to -- ZSM-5 --

Signed and Sealed this

Nineteenth Day of February, 1991

*Attest:*

HARRY F. MANBECK, JR.

*Attesting Officer*      *Commissioner of Patents and Trademarks*